US00PP31708P2

(12) United States Plant Patent
Van Swieten

(10) Patent No.: US PP31,708 P2
(45) Date of Patent: Apr. 28, 2020

(54) *PHALAENOPSIS* ORCHID PLANT NAMED 'PHALGURZON'

(50) Latin Name: ***Phalaenopsis* hybrid**
Varietal Denomination: PHALGURZON

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,969

(22) Filed: Jul. 12, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGURZON', particularly characterized by having copper, striped and netted flowers with red-purple lips, 1 to 3 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALGURZON'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGURZON'.

The new *Phalaenopsis* plant is a product of a planned breeding program conducted by the inventor in Bleiswijk, the Netherlands. The objective of this breeding program was to create a new *Phalaenopsis* plant with numerous attractive copper, striped and netted flowers with red-purple lips, suitable for potted plant production.

The new *Phalaenopsis* plant 'PHALGURZON' is a result of cross-pollination made by the inventor in July 2010 in Bleiswijk, the Netherlands, of the proprietary female, or seed parent, *Phalaenopsis* hybrid '01-1805' (unpatented) with the proprietary male, or pollen parent, *Phalaenopsis* hybrid 'PHALFYQDHA' (U.S. Plant Pat. No. 27,456).

The new *Phalaenopsis* was selected by the inventor as a single plant within the progeny of the stated cross-pollination in a controlled greenhouse in Bleiswijk, the Netherlands, in May 2013. Asexual reproduction of the new *Phalaenopsis* plant by meristem tissue culture since 2016 in Bleiswijk, the Netherlands, has demonstrated that the new variety reproduces true to type with all of the characteristics, as herein described, thinly fixed and retained through successive generations.

Plant Breeder's Rights for this variety have been applied for in the European Union on Apr. 26, 2018, by Applicant who obtained the subject matter disclosed directly from the Inventor. 'PHALGURZON' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALGURZON' as a new and distinct variety of *Phalaenopsis* plant:

1) Copper, striped and netted flowers with red-purple lips;
2) 1 to 3 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
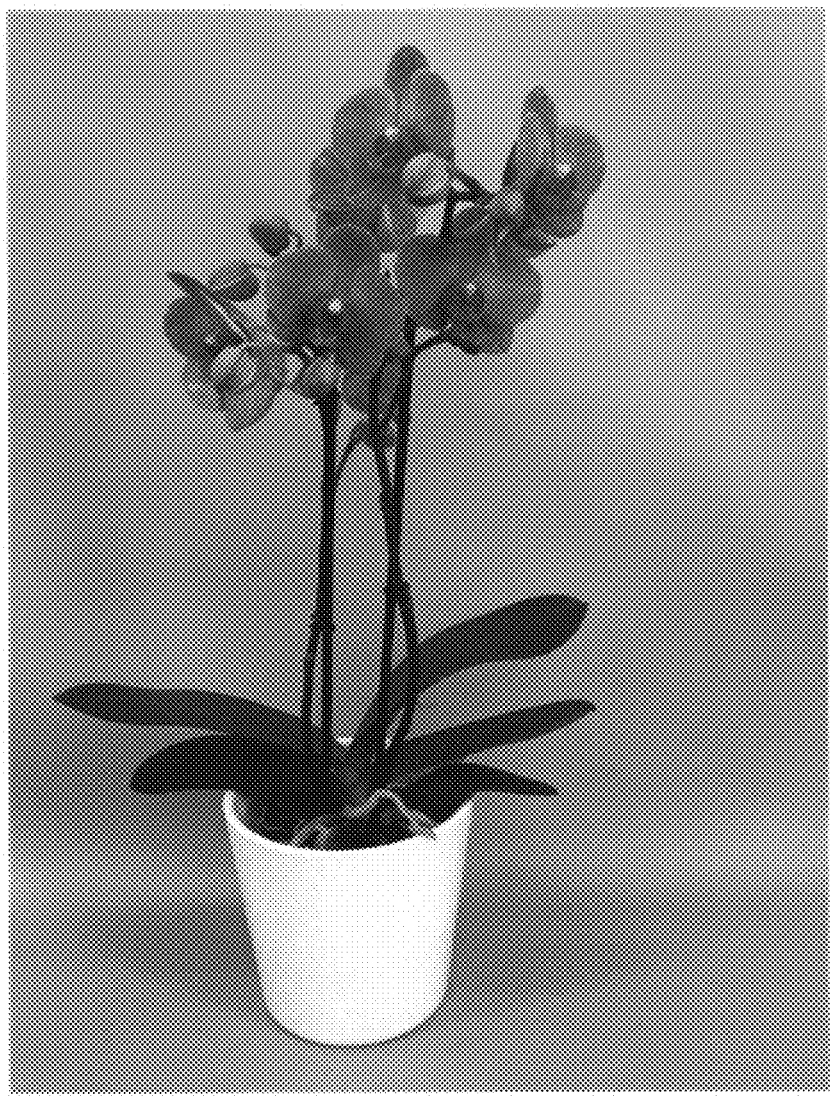
FIG. 1 shows the overall plant habit, including blooms, buds, and foliage of 'PHALGURZON'.
Figure 2:
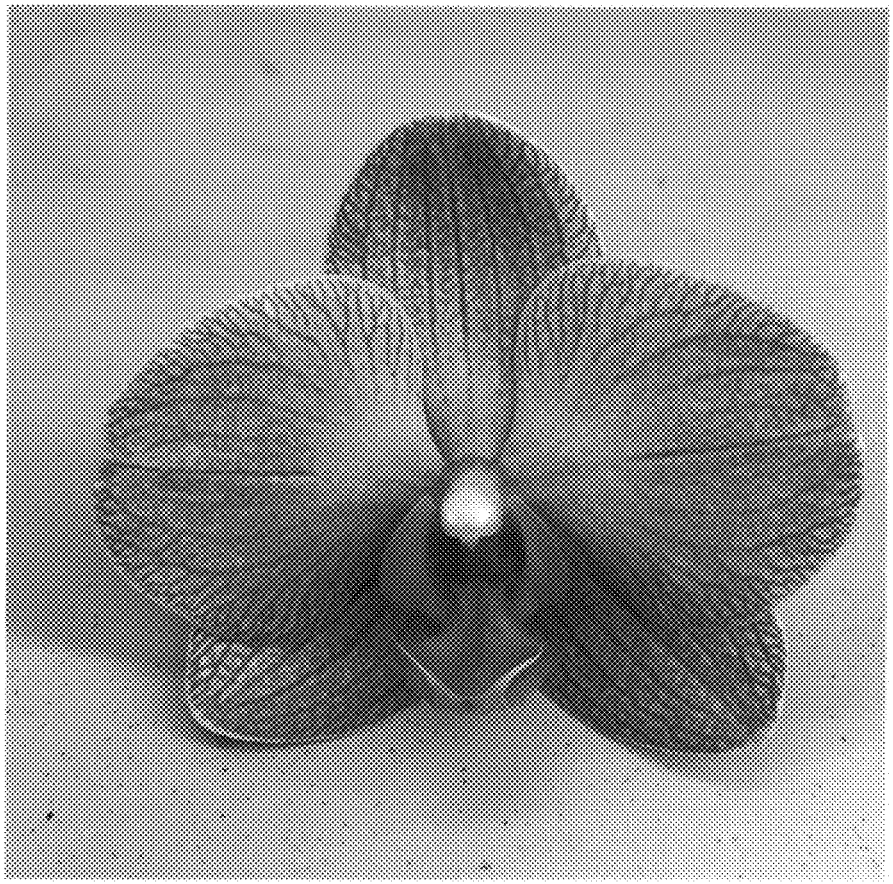
FIG. 2 shows a close-up of a flower of 'PHALGURZON'.
Figure 3:
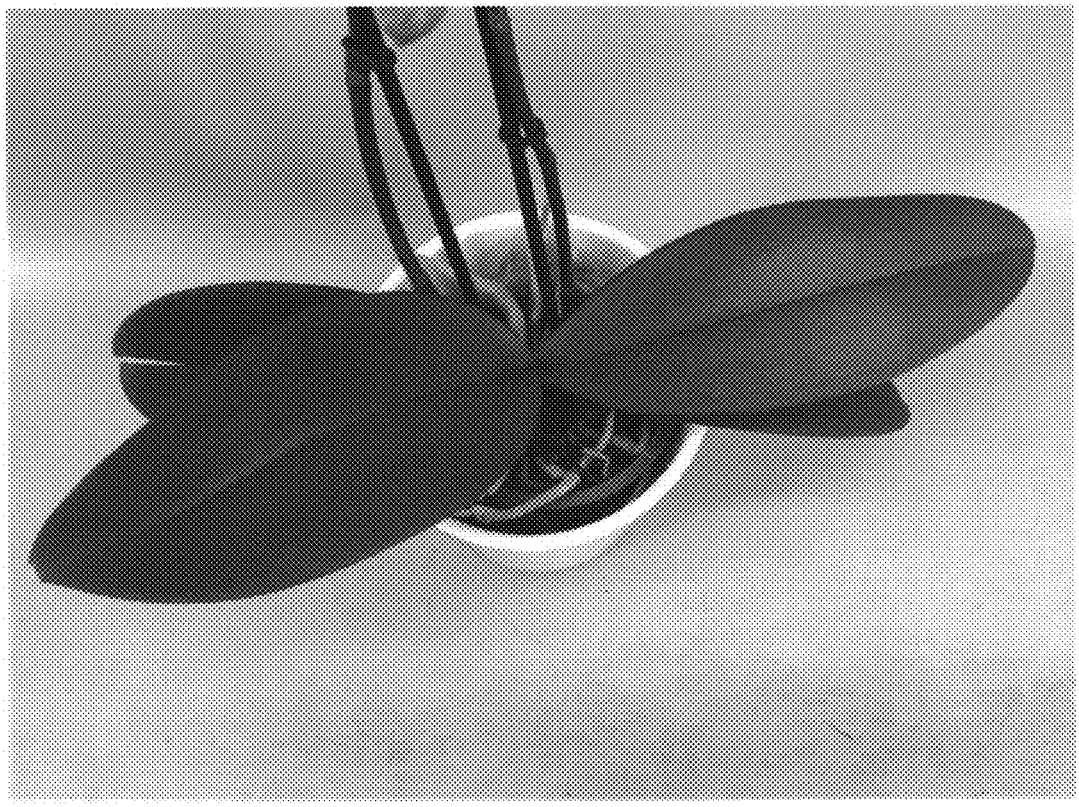
FIG. 3 shows an overhead view of the leaves of 'PHALGURZON'.

The following detailed description sets forth the distinctive characteristics of 'PHALGURZON'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGURZON'.

Parentage:

*Female parent*.—*Phalaenopsis* cultivar '01-1805' (unpatented).

*Male parent*.—*Phalaenopsis* cultivar 'PHALFYQDHA' (U.S. Plant Pat. No. 27,456).

Propagation:

*Type*.—Meristem tissue culture.

Roots:

*Root description*.—Greyed-green (between RHS 190B and 190C) colored roots with branching lateral roots having yellow-green (RHS 144C) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with panicle inflorescence.

*Height (from soil level to top of inflorescence)*.—Approximately 37.0 cm to 42.0 cm.

*Width (measured from leaf tips)*.—About 32.0 cm to 34.0 cm.

*Vigor*.—Moderate.

Leaves:

*Mature leaves*.—Quantity per plant: 7 to 8 leaves are produced before flowering. Length (fully expanded): 18.0 cm to 20.0 cm. Width: 8.0 cm to 9.0 cm. Shape: Oblong. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 146A. Lower surface: RHS 146B. Texture (both upper and lower surfaces): Rough. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—9 to 14.

*Length*.—37.0 cm to 42.0 cm.

*Diameter*.—5.0 mm to 6.0 mm.

*Strength*.—Strong.

*Aspect*.—Upright to slightly pendant.

*Texture*.—Smooth.

*Color*.—Mix of green (RHS 146B) and brown (RHS N199B).

*Internode length*.—3.0 cm to 5.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 3.

*Inflorescence size*.—Height (from base to tip): 180.0 mm to 220.0 mm.

*Flowering time*.—First flowers can be expected 10 to 11 months after planting in a 12-cm pot.

*Flower*.—Height: 57.0 mm to 62.0 mm. Diameter: 67.0 mm to 72.0 mm. Depth of lip: 17.0 mm to 19.0 mm.

*Flower longevity*.—On the plant: 12 to 17 weeks.

*Fragrance*.—Absent.

*Flower bud*.—Average size: Medium to large. Length: 21.0 mm to 23.0 mm. Width: 19.0 mm to 21.0 mm. Shape: Egg shaped. Color: Light yellow-green (RHS 145B) with a touch of purplish-red (RHS 185C).

*Petals*.—Arrangement: Open/free. Shape: Semi-circular. Apex: Rounded asymmetric. Margin: Slightly undulated. Length (from base to tip): 31.0 mm to 33.0 mm. Width: 35.0 mm to 37.0 mm. Position of the broadest part of the petal: At the base. Color (when fully opened): Upper surface: Basic color: Greenish-yellow (RHS 2B). Over color: Purplish-red (RHS 184C) at the base; red striped (RHS 181B) and slightly netted (RHS 181A) at the margin. Lower surface: Basic color: Light yellow-green (RHS 154D). Over color: Diluting red stripes (RHS 182B).

*Dorsal sepal*.—Shape: Elliptic. Apex: Rounded symmetric. Margin: Entire. Length (from base to tip): 32.0 mm to 34.0 mm. Width: 26.0 mm to 28.0 mm. Color (when fully opened): Upper surface: Basic color: Light yellow-green (RHS 2C). Over color: Purplish-red (RHS 186A to 186B) at the base; red striped (RHS 181B) and netted (RHS 181A). Lower surface: Basic color: Greenish-yellow (RHS 151A). Over color: Diluting red stripes (RHS 182A to 182B).

*Lateral sepals*.—Shape: Ovate. Apex: Obtuse asymmetric. Margin: Entire. Length (from base to tip): 32.0 mm to 34.0 mm. Width: 23.0 mm to 25.0 mm. Color (when fully opened): Upper surface: Basic color: Greenish-yellow (RHS 2B). Over color: Red (RHS 184B) at the base; red stripes and netting (RHS 184A). Lower surface: Basic color: Greenish-yellow (RHS 151A). Over color: Diluting red stripes (RHS 182B).

*Labellum (lip)*.—Whiskers: Present. Length of whiskers: 5.0 mm to 7.0 mm. Color of whiskers: Reddish-purple (RHS N78B) at the base and orange-yellow (RHS 163B) toward the tip. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 13.0 mm to 15.0 mm. Width: 8.0 mm to 10.0 mm. Color: Light yellow (RHS 12C) with red stripes (RHS 185A) at the base; red (RHS 185A) on one side; reddish-orange (RHS 174B) in the middle and purplish-red (RHS 70A) toward the other side.

*Apical lobe*.—Shape: Trullate. Margin: Entire. Length: 18.0 mm to 20.0 mm. Width: 15.0 mm to 17.0 mm. Color: Slightly yellow (RHS 12A) at the base; red (RHS 185A) and purplish-red (RHS 70A) toward whiskers.

*Callus*.—Average size: Small. Height: 3.0 mm to 4.0 mm. Length: 4.0 mm to 5.0 mm. Width: 3.0 mm to 4.0 mm. Color: Reddish-orange (RHS 171A) with yellow spots (RHS 13A).

Reproductive organs:

*Column*.—Length: 8.0 mm to 10.0 mm. Diameter: 5.0 mm to 6.0 mm. Color: Light reddish-purple (RHS N78D).

*Pollinia*.—Quantity: 2. Diameter: 0.9 mm to 1.1 mm. Color: Orange (RHS 24A).

*Ovary*.—Length: 10.0 mm to 12.0 mm. Diameter: 2.5 mm to 2.8 mm. Color: Light yellow-green (RHS 145C) and light yellow-green (RHS 145D) toward the flower.

*Pedicel*.—Length: 37.0 mm to 40.0 mm. Diameter: 2.9 mm to 3.2 mm. Color: Yellow-green (RHS 145A) and light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGURZON' differs from female parent plant '01-1805' (unpatented) in that 'PHALGURZON' has striped and netted flowers, trullate apical lobes, weakly spatulate lateral lobes, light reddish-purple columns, and whiskers, whereas '01-1805' has flecked flowers, rhombic apical lobes, oblong lateral lobes, white columns, and no whiskers. Additionally, 'PHALGURZON' has larger flowers than '01-1805'.

'PHALGURZON' differs from male parent plant 'PHALFYQDHA' (U.S. Plant Pat. No. 27,456) in that 'PHALGURZON' has weakly spatulate lateral lobes, reddish-orange calluses, light reddish-purple columns, and flowers with a striped and netted pattern, whereas 'PHALFYQDHA' has spatulate lateral lobes, yellow calluses, white columns, and flowers with a centered pattern. Additionally, 'PHALGURZON' has smaller flowers than 'PHALFYQDHA'.

'PHALGURZON' is most similar to the commercial *Phalaenopsis* plants named 'PHALDIQYK' (U.S. Plant Pat. No. 27,342) and 'PHALKUZEL' (U.S. Plant patent application Ser. No. 16/350,272). 'PHALGURZON' differs from the commercial variety 'PHALDIQYK' in that 'PHALGURZON' has reddish-orange calluses and trullate apical lobes, whereas 'PHALDIQYK' has yellow calluses and rhombic apical lobes. Additionally, 'PHALGURZON' has smaller flowers than 'PHALDIQYK'.

'PHALGURZON' differs from the commercial variety 'PHALKUZEL' in that 'PHALGURZON' has reddish-orange calluses, trullate apical lobes, and flowers with a striped and netted pattern, whereas 'PHALKUZEL' has yellow calluses, rhombic apical lobes, and flowers with a shaded and small center pattern. Additionally, 'PHALGURZON' has smaller flowers than 'PHALKUZEL'.

I claim:

1. A new and distinct variety of *Phalaenopsis* plant named 'PHALGURZON', substantially as described and illustrated herein.

* * * * *